(12) United States Patent
Ishimaru

(10) Patent No.: US 9,482,576 B2
(45) Date of Patent: *Nov. 1, 2016

(54) SPECTROSCOPIC MEASUREMENT DEVICE HAVING TRANSMISSIVE OPTICAL MEMBER WITH A SLOPED FACE

(71) Applicant: NATIONAL UNIVERSITY CORPORATION KAGAWA UNIVERSITY, Takamatsu-shi, Kagawa (JP)

(72) Inventor: Ichiro Ishimaru, Takamatsu (JP)

(73) Assignee: NATIONAL UNIVERSITY CORPORATION KAGAWA UNIVERSITY, Takamatsu-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/668,106

(22) Filed: Mar. 25, 2015

(65) Prior Publication Data

US 2015/0198483 A1    Jul. 16, 2015

Related U.S. Application Data

(62) Division of application No. 14/430,658, filed as application No. PCT/JP2013/076871 on Oct. 2, 2013.

(30) Foreign Application Priority Data

Oct. 5, 2012 (JP) ................. 2012-223460

(51) Int. Cl.
G01J 3/02 (2006.01)
G01J 3/453 (2006.01)
(Continued)

(52) U.S. Cl.
CPC ............ *G01J 3/0208* (2013.01); *A61B 5/1455* (2013.01); *G01J 3/021* (2013.01); *G01J 3/4531* (2013.01); *G01J 3/4535* (2013.01); *A61B 2562/0233* (2013.01); *G01J 3/2803* (2013.01)

(58) Field of Classification Search
CPC ...... A61B 5/14; G01J 3/4535; G01J 3/0208; G01J 3/021; G01J 3/2803
See application file for complete search history.

(56) References Cited

U.S. PATENT DOCUMENTS 6,559,952 B1   5/2003 Bokor et al.
6,687,010 B1 * 2/2004 Horii ............... G01B 9/0201
                                                      356/479
(Continued)

FOREIGN PATENT DOCUMENTS

CN    1800835 A    7/2006
CN    102359818 A    2/2012
(Continued)

OTHER PUBLICATIONS

Sato et al., "Proposal of One-Shot-Type Spectroscopic-Tomography for Non-Invasive Medical-Measurement." retrieved online: Dec. 27, 2013 <URL:http//proceedings.spiedigitallibrary.org/data/Conference/SPIEP/74989/879801.pdf>.
(Continued)

*Primary Examiner* — Hwa Lee
(74) *Attorney, Agent, or Firm* — Oliff PLC

(57) ABSTRACT

A spectroscopic measurement device includes: a dividing optical system for dividing a measurement beam emitted from each of a plurality of measurement points located within a measurement area of an object to be measured, into a first measurement beam and a second measurement beam; an imaging optical system; an optical path length difference providing means; a detector including a plurality of pixels; a processor for acquiring an interferogram of a measurement point of the object to be measured; a conjugate plane imaging optical system located between the object to be measured and the dividing optical system; and a periodicity providing means located on the conjugate plane.

7 Claims, 11 Drawing Sheets

(51) Int. Cl.
  *A61B 5/1455*    (2006.01)
  *G01J 3/28*      (2006.01)

(56) References Cited

U.S. PATENT DOCUMENTS

| 8,154,732 | B2 | 4/2012 | Bodkin et al. |
| 2013/0215428 | A1 | 8/2013 | Ishimaru |

FOREIGN PATENT DOCUMENTS

| DE | 19650507 C1 | 12/1997 |
| EP | 2 615 436 A1 | 7/2013 |
| JP | H04-264205 A | 9/1992 |
| JP | 2008-309707 A | 12/2008 |
| JP | 2012-181060 A | 9/2012 |
| WO | 2012/033096 A1 | 3/2012 |

OTHER PUBLICATIONS

Jan. 11, 2016 Search Report issued in European Patent Application No. 15169062.5.
Jan. 25, 2016 Office Action issued in Chinese Patent Application No. 2016012001342750.
Mar. 15, 2016 Search Report issued in European Patent Application No. 13844486.4.
Uraki et al.; "Proposal of the One-shot real-time Fourier spectroscopic imaging;" Optics & Photonics Japan 2010 Extended Abstracts; Nov. 8, 2010; pp. 84-85; XP008170256.
Junttila; "Stationary Fourier-transform spectrometer;" Applied Optics; Optical Society of America, Washington, DC; US; vol. 31, No. 21, Jul. 20, 1992; pp. 4106-4112; XP000289230.
Jan. 25, 2016 Office Action issued in Chinese Patent Application No. 201380052250.3.
Apr. 21, 2016 Office Action issued in Korean Patent Application No. 10-2015-7008521.
Jan. 20, 2016 Office Action issued in U.S. Appl. No. 14/430,658.
Sato et al., "Proposal of One-Shot-Type Spectroscopic-Tomography for Non-Invasive Medical-Measurement." retrieved online: Dec. 27, 2013 <URL:http//proceedings.spiedigitallibrary.org/data/Conference/SPIEP/74989/879801.pdf>.
Jan. 21, 2014 International Search Report issued in International Application No. PCT/JP2013/076871.
Apr. 7, 2015 International Preliminary Report on Patentability issued in International Application No. PCT/JP2013/076871.

\* cited by examiner

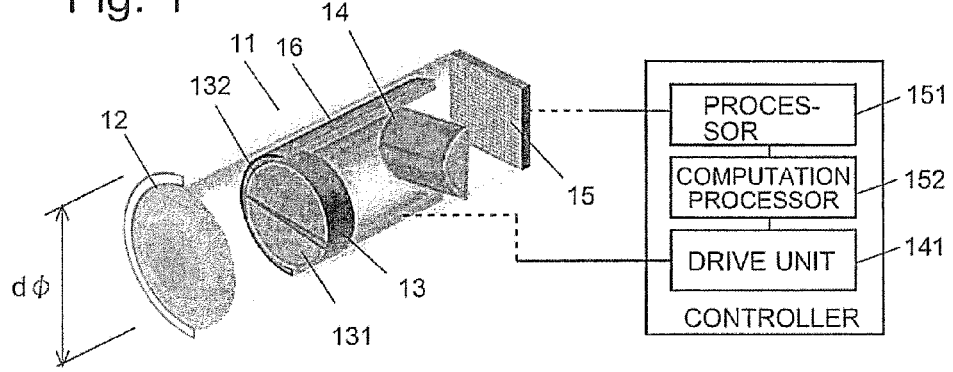
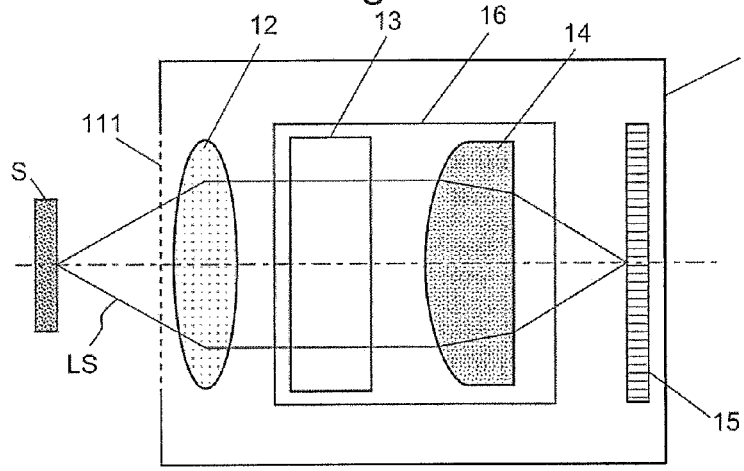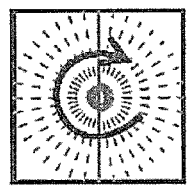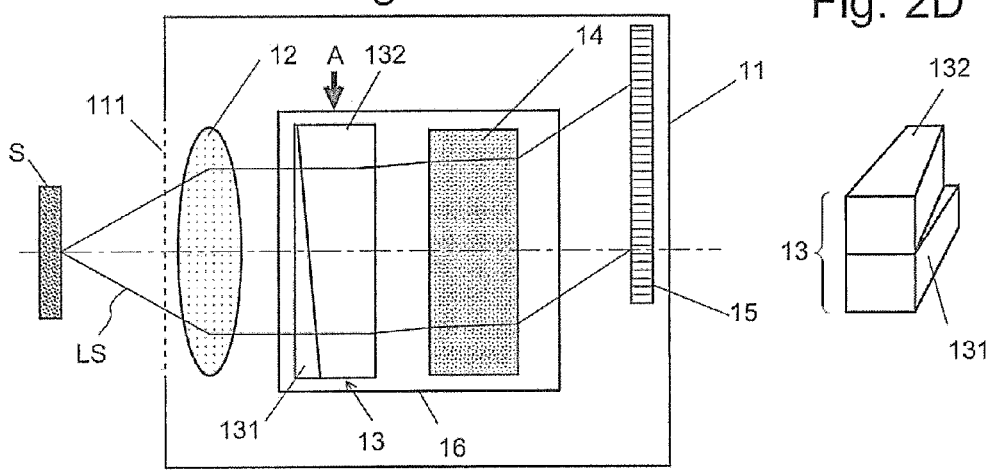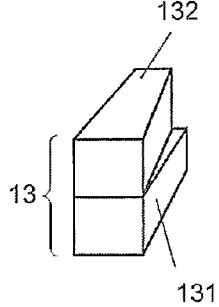

TRANSMISSIVE-TYPE
INCLINATION OF GLASS BODY
=TRANSLATION OF OPTICAL AXIS

INTERFERENCE WITH
HIGH VISIBILITY

REFLECTIVE-TYPE
INCLINATION OF MIRROR
=ROTATION OF OPTICAL AXIS

NO INTERFERENCE

Fig. 8
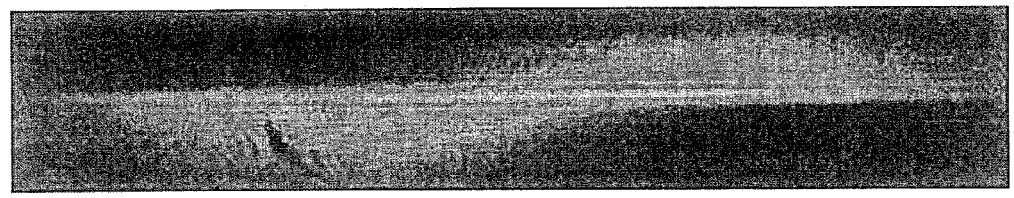
Fig. 9
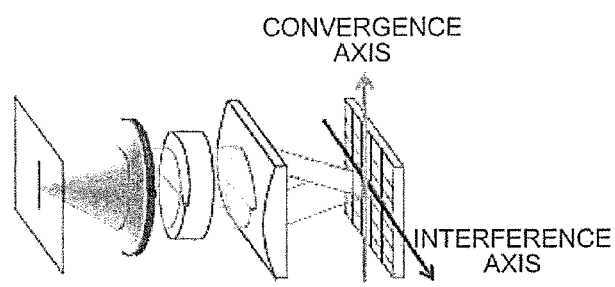
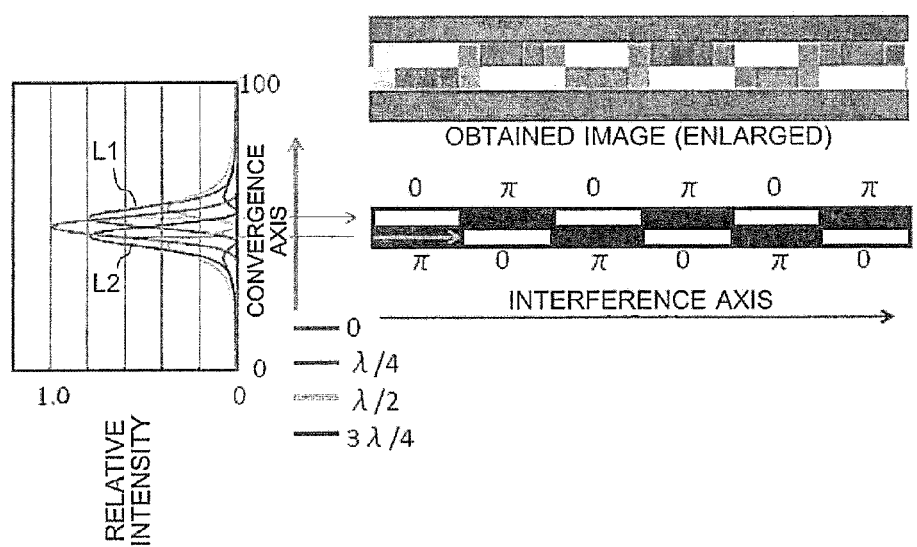

SPECTROSCOPIC MEASUREMENT DEVICE HAVING TRANSMISSIVE OPTICAL MEMBER WITH A SLOPED FACE

This is a Division of application Ser. No. 14/430,658 filed Mar. 24, 2015, which in turn is a National Phase of Application No. PCT/JP2013/076871 filed Oct. 2, 2013, which claims the benefit of Japanese Application No. 2012-223460 filed Oct. 5, 2012. The disclosures of the prior applications are hereby incorporated by reference herein in their entirety.

TECHNICAL FIELD

The present invention relates to a spectroscopic measurement device, and more specifically, to a spectroscopic measurement device that can non-invasively measure biological components, such as blood sugar and blood cholesterol.

BACKGROUND ART

A control of amounts of biological components in blood, such as blood glucose (blood sugar) and blood cholesterol, is important to prevent and treat various diseases, such as diabetes and hyperlipidemia. However, to measure amounts of biological components in blood, a small amount of blood usually needs to be drawn, which is painful for an individual. Blood drawing also requires troublesome tasks, such as sterilization of the blood drawing area and proper treatment of consumables, so that frequent blood drawing for the measurement of amounts of biological components for preventive reasons or other purposes is apt to be averted.

To address this problem, a non-invasive measurement device which measures amounts of biological components without drawing blood has been proposed (Patent Literature 1). In this device, light is cast onto a biological tested area and the spectral characteristics of light (object light) emitted from biological components inside the tested area in response to the cast light is analyzed to identify the biological component. Specifically, object light, including transmitted light and diffused/scattered light, generated from each of the bright points which optically form biological components is guided through an objective lens to a phase shifter composed of a fixed mirror unit and a movable mirror unit, and object beams reflected from the two mirror units are made to interfere with each other on an imaging plane. The movable mirror unit is moved by a piezo element or the like, and a phase difference corresponding to the moving distance of the movable mirror unit is given to the object beams reflected from the fixed mirror unit and the movable mirror unit. The intensity of the interference light produced from the two beams changes with their phase difference, forming a so-called interferogram. This interferogram is Fourier-transformed to obtain spectral characteristics (spectrum) of the object light.

CITATION LIST

Patent Literature

Patent Literature 1: JP 2008-309707 A

SUMMARY OF INVENTION

Technical Problem

However, the following problems occur in the case of measuring amounts of biological components by the previously described measurement device.

The first problem is that the aforementioned measurement device requires high accuracy in the placement angles of both the fixed and movable mirror units. In this measurement device, the object beams reflected from the two mirror units are made to interfere with each other and the spectral characteristics are obtained based on a change in the intensity of the interference light. The placement angles of the reflecting surfaces of the two mirror units determines the imaging position on the interference plane of the object beams reflected from those surfaces. Therefore, to make the object light correctly form an image and interfere at the predetermined position, it is necessary to accurately set the angular position of the reflecting surfaces of the two mirror units. Even if the reflecting surfaces of the two mirror units are correctly oriented at the stage of assembling the device, the relative angle of the reflecting surfaces of the two mirror units may later change due to various factors, such as a disturbance (e.g. a change in the temperature, humidity or other environmental conditions) or an error in the motion of the movable mirror unit. In such a case, the interference phenomenon of the object beams reflected from the two mirror units does not occur at the predetermined imaging position, and the spectral characteristics of the object light cannot be obtained.

The second problem is that the distribution of the amount of interference light on the imaging plane is affected by the difference in the diffraction angle due to the texture (surface condition) of the tested area or other factors. That is to say, the distribution of the amount of object light on the imaging plane is affected by not only the absorbance distribution which depends on the concentration distribution of the amounts of biological components, but also the refractive-index distribution or other properties of the tested area along with the difference in the optical texture at the location where the object light passes, so that the concentration distribution of the amounts of biological components cannot be correctly measured.

Furthermore, in the case of spatially coherent light, no higher-order light will be generated from a sample which has practically no texture, but only the zeroth-order light results. For example, in the case of Koehler illumination, the zeroth-order light reaches the objective lens in the form of a collimated beam and converges on the optical Fourier-transform plane. This means that its wave front cannot be divided by the two mirrors and the spectral characteristics cannot be obtained.

A problem to be solved by the present invention is to provide a spectroscopic measurement device which can reduce influences on the device from disturbances, internal mechanical errors or other factors. Another problem to be solved by the present invention is to provide a spectroscopic measurement device which can correctly obtain spectral characteristics of a tested area both in the case where an optically disturbing element is present near the tested area and in the converse case where the spatial change is unnoticeable (the spatial frequency is low).

Solution to Problem

A spectroscopic measurement device according to the first aspect of the present invention includes:

a) a dividing optical system for dividing a measurement beam emitted from each of a plurality of measurement points located within a measurement area of an object to be measured, into a first measurement beam and a second measurement beam;

b) an imaging optical system for making the first measurement beam and the second measurement beam interfere with each other;

c) an optical path length difference providing means for providing a continuous distribution of an optical path length difference between the first measurement beam and the second measurement beam;

d) a detector including a plurality of pixels for detecting intensity distribution of the interference lights corresponding to the continuous distribution of the optical path length;

e) a processor for acquiring an interferogram of a measurement point of the object to be measured based on the light intensity distribution of the interference light detected by the detector, and for Fourier-transforming this interferogram to obtain a spectrum;

f) a conjugate plane imaging optical system located between the object to be measured and the dividing optical system, the conjugate plane imaging optical system having a conjugate plane shared with the dividing optical system; and g) a periodicity providing means located on the conjugate plane, for giving a spatially periodic modulation to the measurement beams emitted from the plurality of measurement points.

The spectroscopic measurement device according to the first aspect of the present invention may alternatively adopt a configuration including:

a) a fixed reflection unit, and a movable reflection unit which is arranged next to the fixed reflection unit and which is movable in the direction of an optical axis;

b) an incident optical system for making a measurement beam emitted from each of a plurality of measurement points located within a measurement area of an object to be measured enter the fixed reflection unit and the movable reflection unit;

c) an imaging optical system for producing an interference light from the measurement beam reflected by the fixed reflection unit and the measurement beam reflected by the movable reflection unit, by guiding the two measurement beams to the same point;

d) a light detection unit including a plurality of pixels for detecting intensities of the interference lights each of which is generated from the measurement light emitted from each of the plurality of the measurement points e) a processor for acquiring an interferogram of the two measurement beams based on a change in the intensity of the interference light detected by the interference light detector, by moving the movable reflection unit;

f) a conjugate plane imaging optical system located between the object to be measured and the incident optical system, the conjugate plane imaging optical system having a conjugate plane shared with the incident optical system; and g) a periodicity providing means located on the conjugate plane, for giving a spatially periodic modulation to the measurement beams emitted from the plurality of measurement points.

In the spectroscopic measurement device according to the first aspect of the present invention, a periodicity providing means is placed on a plane conjugate with the measurement points (object surface) so as to obtain an interference light from light to which a spatial periodic modulation is given. As a result, even if the sample has practically no texture, higher-order diffraction light can be generated and interference light can be obtained. Furthermore, the influence of the texture of the measurement points of the object to be measured on the distribution of the amount of light on the Fourier-transform plane can be eliminated by superposing a certain spatial periodicity on the real image formed on the conjugate plane.

A spectroscopic measurement device according to the second aspect of the present invention aimed at solving the previously described problem includes:

a) a transmissive optical member composed of a first transmissive part having an entrance face and an exit face parallel to each other and a second transmissive part located next to the first transmissive part and shaped like a wedge having an entrance face and an exit face one of which is sloped relative to the other, with either the entrance face or the exit face of the second transmissive part lying on the same plane as either the entrance face or the exit face of the first transmissive part;

b) an objective lens for collimating a measurement beam emitted from each of a plurality of measurement points located within a measurement area of an object to be measured and for making the collimated beam enter the first transmissive part and the second transmissive part;

c) a cylindrical lens having an axis parallel to the line of intersection of the entrance face of the first transmissive part and the boundary surface between the first transmissive part and the second transmissive part, for receiving a first measurement beam transmitted through the first transmissive part and a second measurement beam transmitted through the second transmissive part;

d) a detector including a plurality of pixels for detecting an intensity distribution of an interference light produced from the first measurement beam and the second measurement beam entering the cylindrical lens; and e) a processor for acquiring an interferogram of the measurement points of the object to be measured based on the intensity distribution of the interference light detected by the detector, and for Fourier-transforming the interferogram to obtain a spectrum.

In the spectroscopic measurement device according to the second aspect, a portion of the measurement beam which has entered the objective lens enters the first transmissive part and subsequently enters the cylindrical lens as the first measurement beam. The remainder of the measurement beam which has entered the objective lens enters the second transmissive part and subsequently enters the cylindrical lens as the second measurement beam. Since the second transmissive part consists of a wedge-shaped optical member, the first and second measurement beams enter the cylindrical lens with a phase difference, forming an interference light on the imaging plane of the cylindrical lens. From the intensity distribution of this interference light, an interferogram of the measurement points of the object to be measured can be acquired. By Fourier-transforming this interferogram, a spectrum of the measurement point can be obtained.

In the spectroscopic measurement device according to the second aspect, the objective lens, the optical member, the cylindrical lens and the detector can be linearly arranged; accordingly, by containing these components in a single tubular case, a compact and disturbance-proof spectroscopic measurement device can be provided.

Advantageous Effects of the Invention

In the spectroscopic measurement device according to the first aspect of the present invention, a periodicity providing means is placed on a plane conjugate with the measurement points (object surface) so as to obtain an interference light from light to which a spatial periodic change is given. As a result, even if the sample has practically no texture, higher-order diffraction light can be generated and interference light can be obtained. Furthermore, the influence of the texture of the measurement points of the object to be measured on the distribution of the amount of light on the Fourier-transform plane can be eliminated by superposing a certain spatial periodicity on the real image formed on the conjugate plane.

In the spectroscopic measurement device according to the second aspect of the present invention, a transmissive optical member composed of the first transmissive part and the second transmissive part is used to divide the measurement beam emitted from a measurement point of the object to be measured into two beams and to simultaneously provide a continuous optical path length difference between the two measurement beams. Accordingly, unlike the conventional measurement device in which the optical path length difference is provided by moving a movable mirror unit, the placement angles of the first and second transmissive parts can be easily set, and an interference light of the first and second measurement beams can be easily obtained. Furthermore, a system which divides the measurement beam into two by reflecting the measurement beam using two reflecting surfaces is susceptible to a disturbance, since the direction of the reflected beams changes with a change in the inclination of the reflecting surfaces. By contrast, in a system which divides the measurement beam into two by making the measurement beam pass through two transmissive parts as in the present invention, a change in the inclination of the entrance and exit faces of the transmissive parts does not cause a change in the direction of the exiting beams unless the direction of the incident beam changes. Therefore, this system is less susceptible to the influence of any type of disturbance.

BRIEF DESCRIPTION OF DRAWINGS

FIG. 1 is an external perspective view of a spectroscopic measurement device according to the first embodiment of the present invention.

FIG. 2A is a schematic side view of a spectroscopic measurement device, FIG. 2B is a top view of the same device, FIG. 2C is a conceptual diagram of an interference light obtained by rotating an inner case, and FIG. 2D is a perspective view of a transmissive phase shifter viewed from the side indicated by arrow A in FIG. 2B.

FIG. 8 is an interference image formed on the light-receiving surface of a two-dimensional array device.

FIG. 9 is an explanatory diagram of an interference fringe to be obtained.

DESCRIPTION OF EMBODIMENTS

Figure 3:
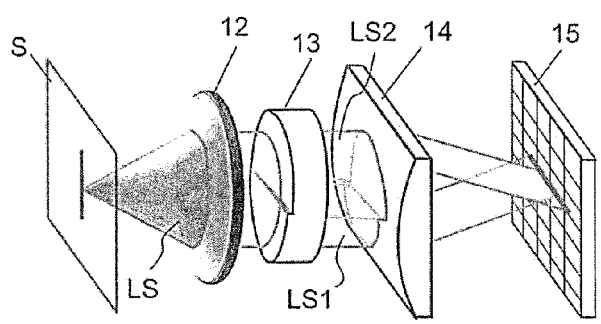
FIG. 3 is an explanatory diagram of the light path of a first measurement beam and a second measurement beam.

Specific embodiments of the present invention are hereinafter described with reference to the attached drawings.
First Embodiment FIG. 1 shows an external perspective view of a spectroscopic measurement device according to the first embodiment of the present invention. This spectroscopic measurement device consists of a tubular case 11 in which the following components are linearly arranged: an objective lens 12, a transmissive phase shifter 13, a cylindrical lens 14 which is an imaging lens, and a two-dimensional array device 15, such as a two-dimensional CCD camera (which corresponding to the detector of the present invention). The case 11 has a window 111 formed at the end portion where the objective lens 12 is located. A measurement beam emitted from an object S to be measured (see FIG. 2) is introduced through this window 111 into the case 11 and made to enter the transmissive phase shifter 13 through the objective lens 12.

The transmissive phase shifter 13 and the cylindrical lens 14 are fixed to a tubular inner case 16 which is fitted in the case 11 in a rotatable manner. The inner case 16 can be rotated by a drive unit 141, such as a supersonic motor or solenoid. With the rotation of this inner case 16, the transmissive phase shifter 13 and the cylindrical lens 14 rotate together as one unit.

For example, the two-dimensional array device 15 consists of a two-dimensional CCD camera and is configured so that the light-receiving surface of the two-dimensional array device 15 is located on the imaging plane of the cylindrical lens 14. The detection signals of the two-dimensional array device 15 are sent to a processor 151. The processor 151 acquires an interferogram from the detection signals of the two-dimensional array device 15. This interfero gram is mathematically Fourier-transformed by a computation processor 152. As a result, a spectral characteristic (spectrum) showing the relative intensity at each wavelength of the measurement light is obtained.

The transmissive phase shifter 13 consists of a first transmissive part 131, which is a semicircular transmissive optical member, and a second transmissive part 132, which is also a semicircular transmissive optical member, forming an approximately cylindrical body as a whole. The first transmissive part 132 consists of an optical member having a uniform thickness with an entrance face and an exit face parallel to each other. By contrast, the second transmissive part 132 consists of a wedge-shaped optical member having an entrance face which is inclined relative to that of the first transmissive part 131 and an exit face which lies on the same plane as that of the first transmissive part 131. In the present embodiment, the entrance face of the second transmissive part 132 is inclined so that the thickness of the second transmissive 132 at the boundary surface between the first transmissive part 131 and the second transmissive part 132 gradually decreases from one end to the other.

The inclination angle of the entrance face of the second transmissive part 132 is determined by the amount of phase shift, which is determined by the wavenumber resolution, as well as the spacing of the pixels to be sampled on the two-dimensional array device 15, although a slight error of this angle causes no problem.

The first transmissive part 131 and the second transmissive part 132 may respectively consist of separate optical members, or they may be created from a disc-shaped optical member by working its upper half area into the second transmissive part 132 having the inclined entrance face. Although the previously described spectroscopic measurement device is configured so that the transmissive phase shifter 13 and the cylindrical lens 14 are exclusively rotated, it is possible to adopt the configuration in which the objective lens 12 and/or the two-dimensional array device 15 is also made to rotate with the transmissive phase shifter 13 and the cylindrical lens 14 as one unit.

An optical operation of the previously described measurement device is hereinafter described with reference to FIGS. 2A-4.

A measurement beam LS emitted from one measurement point on an object S to be measured is collimated by the objective lens 12 and enters both the first transmissive part 131 and the second transmissive part 132 of the transmissive phase shifter 13. By passing through the first transmissive part 131 and the second transmissive part 132, the measurement beam is divided into a first measurement beam and a second measurement beam, which enter the cylindrical lens 14. Since the entrance and exit faces of the first transmissive part 131 are parallel to each other, the first measurement beam LS1 which has entered the cylindrical lens 14 converges, with the same phase, on one straight line on the light-receiving surface of the two-dimensional array device 15. On the other hand, since the second transmissive part 132 has its entrance face inclined relative to its exit face, the second measurement beam LS2 enters the cylindrical lens 14 with its wave front inclined along the entrance face, and then falls onto one straight line on the light-receiving surface of the two-dimensional array device 15 with its wave front still similarly inclined.

Therefore, within the interference area of the first and second measurement beams, the optical path length difference between the two beams gradually changes. Since the measurement beam emitted from each measurement point within the linear measurement area of the object S (see FIG. 3) contains various wavelengths of light, the continuous change in the optical path length difference between the first and second measurement beams within the interference area yields a waveform of the intensity distribution of the interference light as shown in graph (b) FIG. 4, which is called the interferogram.

Figure 4:
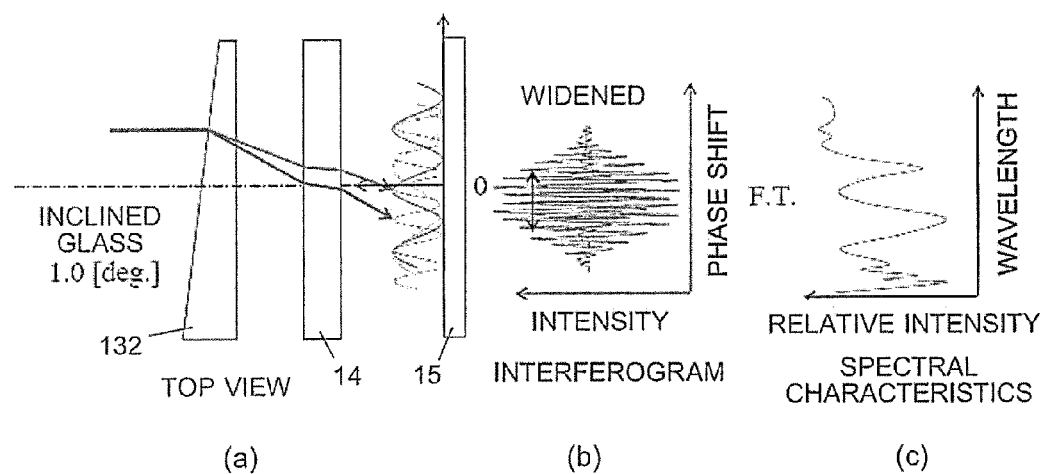
FIG. 4 is an explanatory diagram of a wavelength dispersion which occurs due to the inclination of the entrance face of a second transmissive part, where (a) is a diagram schematically showing a second measurement beam reaching the light-receiving surface of a two-dimensional array device, (b) is an interferogram, and (c) is a spectral characteristic.

In graph (b) in FIG. 4, the vertical axis indicates the amount of phase shift, while the horizontal axis indicates the intensity of the interference light. The amount of phase shift can be calculated from the inclination angle of the second transmissive part 132, the pixel size of the two-dimensional array device 15, the focal length of the cylindrical lens 14 and other parameters. The computation processor 152 performs a Fourier-transform of this interferogram to obtain a spectral characteristic (spectrum) showing the relative intensity at each wavelength of the measurement light emitted from each point of the object S (see graph (c) in FIG. 4). Rotating the inner case 16 by a predetermined angle produces a corresponding rotation of the measurement area of the object S. Accordingly, it is possible to perform a two-dimensional spectral measurement on the entire object S by producing a 360-degree rotation in steps of predetermined angles (see FIG. 2C).

Figure 5:
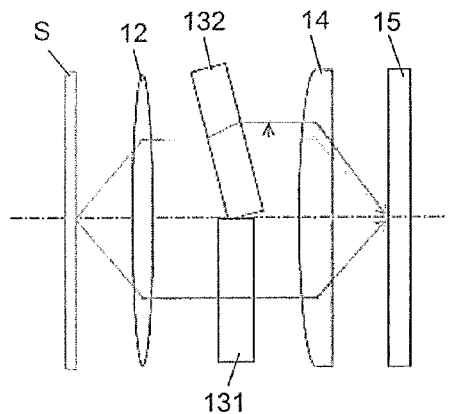
FIG. 5 is a diagram showing a change in the optical path of the measurement beams caused by a change in the placement angle of the transmissive phase shifter.
Figure 6A:
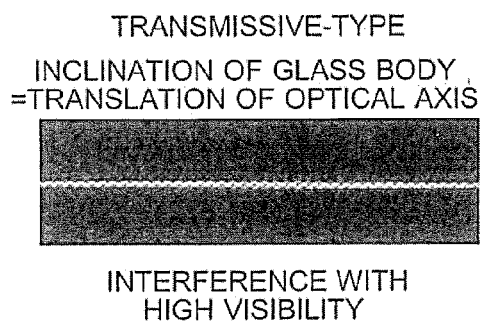
FIG. 6A is an image of the light-receiving surface of the two-dimensional array device observed in the present embodiment.
Figure 6B:
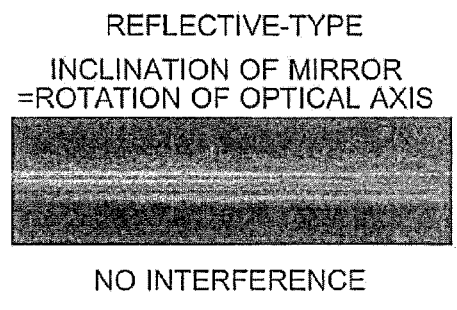
FIG. 6B is an image of the light-receiving surface of the two-dimensional array device observed in a conventional device.

Since the measurement beam (second measurement beam) which has entered the entrance face of the second transmissive part 132 has a different refraction angle for each wavelength, the second measurement beam exiting from the second transmissive part 132 converges on displaced positions due to dispersion. However, after the Fourier transform of the interferogram, this amount of displacement resulting from this dispersion becomes a phase term and hence does not affect the amplitude term. Accordingly, it does not affect the spectral characteristic obtained by the Fourier transform. Actually, a calculation has proved that the amount of displacement is 3.7 μm when the measurement wavelength range is 900 to 1700 nm, the focal length f is 5 mm and the pixel size of the two-dimensional array device is 30 μm. The calculated value is adequately smaller than the pixel size of the two-dimensional array device 15. This result also demonstrates that the influence of the dispersion is small Furthermore, as shown in FIG. 5, in the case of the transmissive phase shifter 13, a change in the placement angle of first transmissive part 131 or the second transmissive part 132 merely causes a parallel translation of the optical path of the first measurement beam or the second measurement beam (as indicated by the arrow in FIG. 5). Accordingly, the first and second measurement beams converge on the predetermined area and forms an interference image with high visibility, so that it is unnecessary to set the first transmissive part 132 and the second transmissive part 132 with high accuracy. By contrast, in the case of a conventional spectroscopic measurement device, a change in the inclination of a reflecting surface causes a change in the direction of the reflected light, i.e. the first measurement beam or the second measurement beam, which may possibly prevent the interference from occurring. For reference, FIG. 6A shows an image of the light-receiving surface of the two-dimensional array device 15 in the spectroscopic measurement device of the present embodiment, and FIG. 6B shows an image of the light-receiving surface of a two-dimensional array device in a conventional spectroscopic measurement device configured using a reflective phase shifter. No interference of the first and second measurement beams occurred in the conventional device.

Figure 7A:
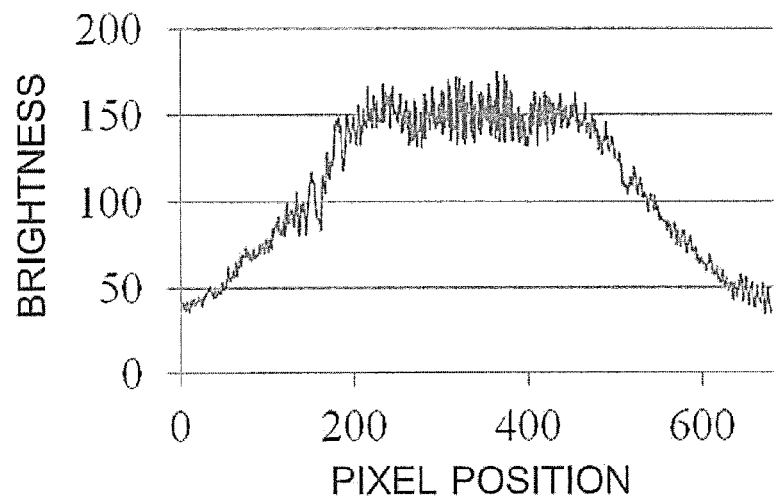
FIGS. 7A and 7B respectively show an interferogram and a relative spectral intensity obtained by casting a laser beam having a wavelength of 532 nm into an objective lens.
Figure 7B:
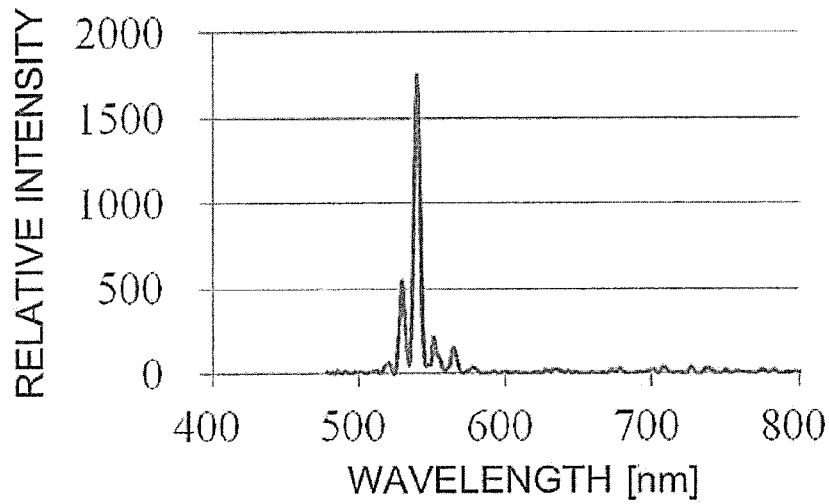

Next, the result of an experiment conducted for evaluating the accuracy of the spectroscopic measurement device according to the present embodiment is shown in FIGS. 7A, 7B and 8. In this experiment, a laser light having a wavelength of 532 nm (a green laser "Verdi G5" marketed by Coherent, Inc. was used as the light source) as the measurement light was made to enter the objective lens 12 through a pinhole (5 µm in diameter) and an interferogram (FIG. 7A) was obtained. This interferogram was Fourier-transformed to obtain a relative spectral intensity (FIG. 7B). The inclination (relative angle) of the entrance face of the second transmissive part 132 relative to that of the first transmissive part 131 in the experiment was 1.0 degree.

As shown in FIG. 7B, the spectrum obtained from the interferogram was a sharp bright-line spectrum having a peak at a wavelength of 532 nm. This demonstrates that the spectral characteristics of the measurement light can be accurately obtained by using the spectroscopic measurement device of the present embodiment.

FIG. 8 shows an interference image on the light-receiving surface of the two-dimensional array device 15 obtained in the present experiment. An enlargement of the central portion of this interferogram has revealed that this portion has a houndstooth pattern. Normally, an interference of two rays of light having a phase difference yields an interference fringe, whereas a houndstooth pattern was formed in the present embodiment. The reason is hereinafter described.

As shown in the upper part of FIG. 9, when the vertical and horizontal axes on the two-dimensional array device are respectively set as the convergence and interference axes, a distribution of the brightness occurs in the direction of the convergence axis due to the convergence limit of the cylindrical lens. This distribution asymmetrically changes with the amount of temporal shift of the phase. In the present embodiment, the phase difference is spatially given by the transmissive phase shift. Therefore, for example, in the case of the curve L1 in the graph shown in the lower left part of FIG. 9, the brightness is higher on the upper side of the convergence axis, whereas in the case of the curve L2, the brightness is higher on the lower side of the convergence axis. As a result, as shown in the lower right part of FIG. 9, the interference pattern does not only show an alternate bright-and-dark pattern extending along the interference axis, but also repeats an alternation of the bright and dark areas in the direction of the convergence axis. It should be noted that the interference fringe in the figure is represented in a binary form of black and white for ease of explanation, where the bright and dark areas are assumed to occur with a phase shift of π.

Second Embodiment

Figure 10:
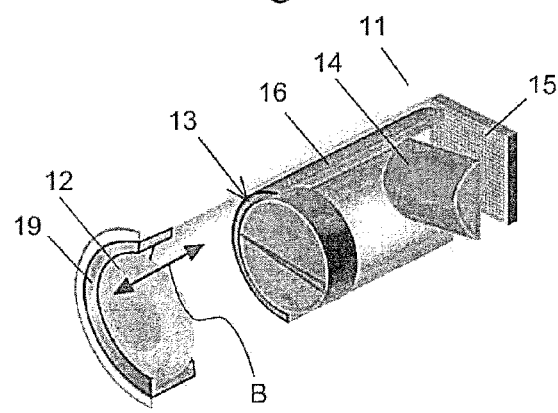
FIG. 10 is an external perspective view of a spectroscopic measurement device according to the second embodiment of the present invention.

FIG. 10 shows a spectroscopic measurement device according to the second embodiment of the present invention. This spectroscopic measurement device differs from the first embodiment in that the objective lens 12 held in the case 11 can be moved within this case 11 in the direction indicated by arrow B. By moving the objective lens 12 in the direction of arrow B in this manner, the focusing plane (the plane including the focusing position) can be moved. Therefore, a three-dimensional spectral measurement can be made by rotating the transmissive phase shifter 13 and the cylindrical lens 14 while moving the objective lens 12. This is due to the characteristic fact that the interferogram, which represents the change in the interference intensity, is formed by only such objective light that contributes to the imaging from the focusing plane, so that the depth of the measurement plane can be limited within the focusing plane.

Third Embodiment

Figure 11:
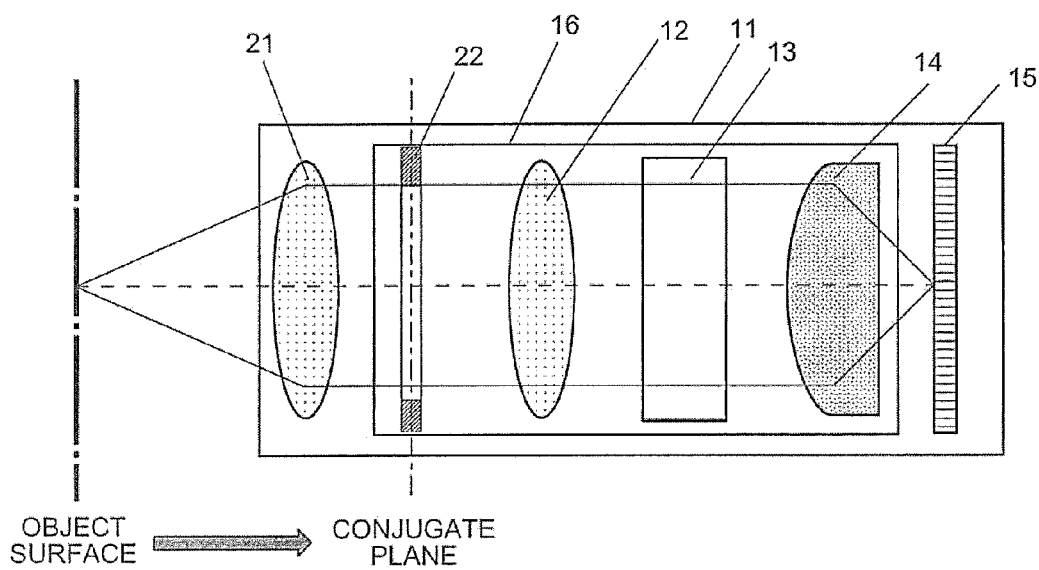
FIG. 11 is a schematic configuration diagram of a spectroscopic measurement device according to the third embodiment of the present invention.

A spectroscopic measurement device according to the third embodiment of the present invention is hereinafter described with reference to FIG. 11. The present spectroscopic measurement device measurement device is characterized in that a relay lens 21 is placed in front of the objective lens 12, and that a phase-type diffraction grating 22 is placed on the conjugate plane of the relay lens 21 and the objective lens 12. The relay lens 21 constitutes the conjugate plane imaging optical system in the present invention. Furthermore, in this spectroscopic measurement device, the inner case 16 contains the phase-type diffraction grating 22, the objective lens 12, the transmissive phase shifter 13 and the cylindrical lens 14.

For example, the phase-type diffraction grating 22 is a transmissive diffraction grating having a sawtooth diffraction plane and gives a periodic phase difference to the light passing through this phase-type diffraction grating 22. That is to say, the phase-type diffraction grating 22 functions as the periodicity providing means in the present invention.

Figure 12:
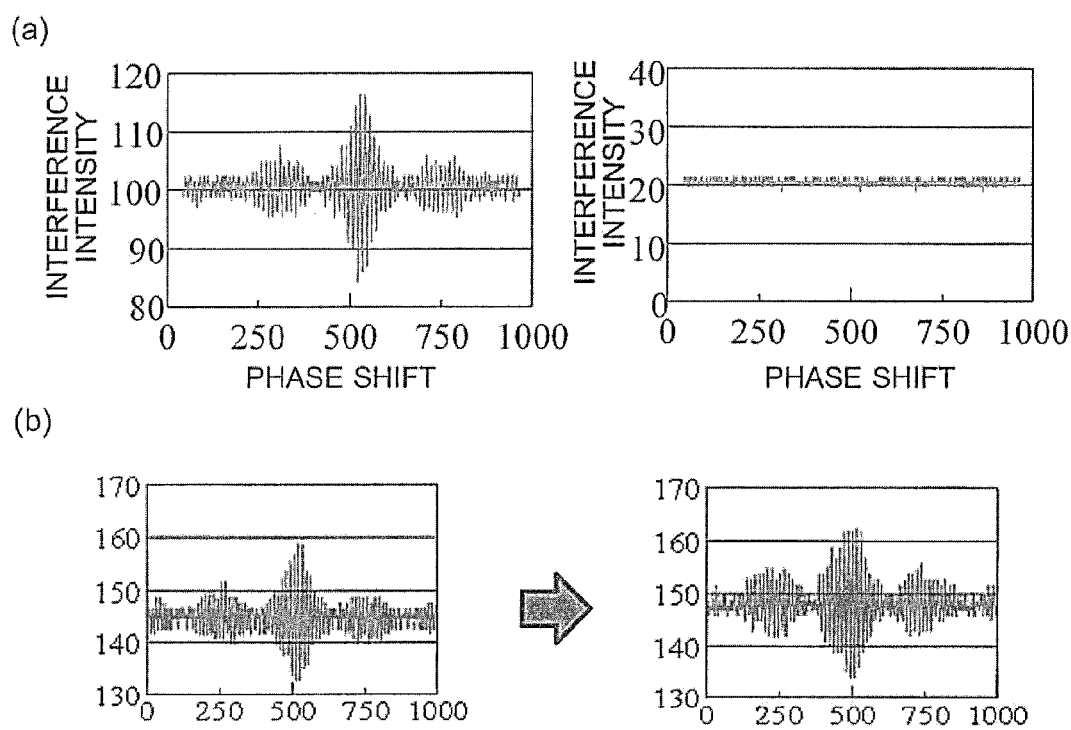
FIG. 12 is a diagram for explaining the effect of the third embodiment.

The effect of the present embodiment is hereinafter described with reference to FIG. 12. The upper part of FIG. 12 shows interferograms observed in the case where the phase-type diffraction grating is not used. Specifically, the left graph is an interferogram of an area with a texture. An interferogram with a high amplitude of intensity is observed, which means that an interference is present. The right graph is an interferogram of an area with no texture. The observed amplitude is almost indiscernible, which means that no interference is present.

The lower part of FIG. 12 shows interferograms observed in the case where the phase-type diffraction grating is used. Specifically, the left graph is an interferogram of an area with a texture. An interferogram with a high amplitude of intensity is observed, which means that an interference is present. The right graph is an interferogram of an area with no texture. Once more, an interferogram with a high amplitude of intensity is observed, which means that an interference is present. Thus, according to the present embodiment, even if the target area has no texture, it is possible to obtain an interference almost comparable to that of a textured area.

In place of the phase-type diffraction grating used in the present embodiment, a slit, or an amplitude-type diffraction grating, may also be used in the case of giving a periodic amplitude distribution to a spatially incoherent light. In this case, the aperture width of the slit should be equal to the convergence limit $2d$ of the objective lens ($d=0.61\lambda/NA$, where $\lambda$ is the wavelength of light and NA is the numerical aperture).

Fourth Embodiment

Figure 13:
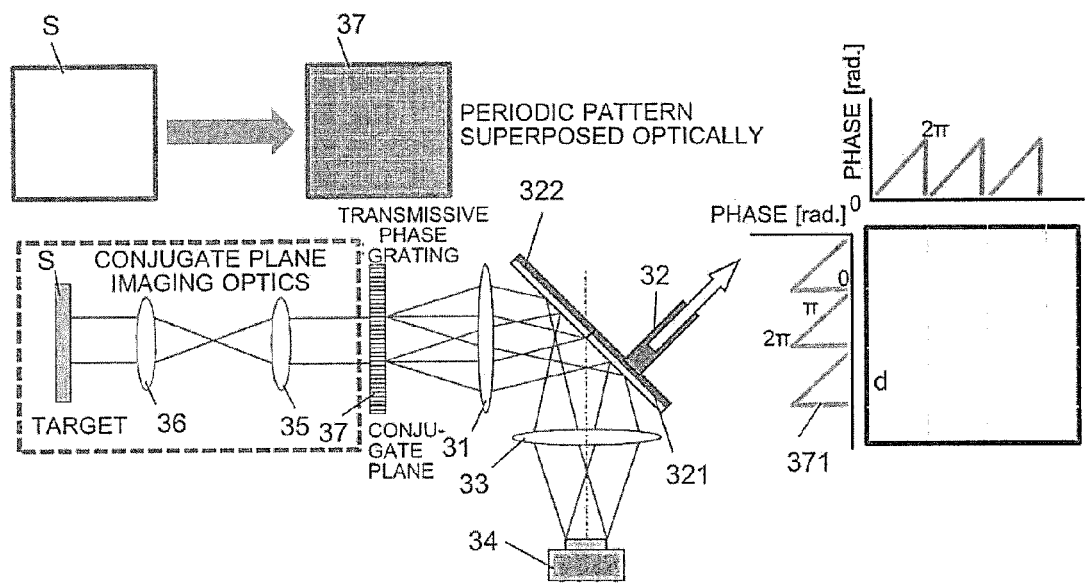
FIG. 13 is a schematic configuration diagram of a spectroscopic measurement device according to the fourth embodiment of the present invention.

FIG. 13 shows the schematic configuration of a spectroscopic measurement device according to the fourth embodiment of the present invention. The present spectroscopic measurement device consists of a conjugate plane imaging optical system and a measurement optical system. The measurement optical system consists of an objective lens 31, a reflective phase shifter 32, an imaging lens 33 and a detector 34. For example, the detector 34 consists of a CCD camera.

The reflective phase shifter 32 consists of a movable mirror unit 321 and a fixed mirror unit 322, and is provided with a drive mechanism 323 for moving the movable mirror unit 321. Both the movable mirror unit 321 and the fixed mirror unit 322 have a surface (reflecting surface) consisting of an optical mirror surface which is optically flat and can reflect a range of wavelengths of light to be measured by the present device. In the present embodiment, the reflective phase shifter 32 corresponds to the optical path length difference providing means.

The conjugate plane imaging optical system consists of: an imaging lens 35 placed in front of the objective lens 31 and at a position between the objective lens 31 and the object to be measured; and an objective lens 36 placed in front of the imaging lens 35. The conjugate plane imaging optical system and the objective lens 31 have a common conjugate plane. A phase-type diffraction grating 37 is placed on this common conjugate plane.

As described earlier, the phase-type diffraction grating 37 gives a periodic phase difference to the light passing through it. Therefore, the measurement light emitted from the object S and forming a real image on the conjugate plane via the objective lens 36 and the imaging lens 35 is given a phase difference in passing through the phase-type diffraction grating 37, and then enters the measurement optical system.

The measurement light which has entered the measurement optical system passes through the objective lens 31 and falls onto the movable mirror unit 321 and the fixed mirror unit 322 of the phase shifter 32. After being reflected by the reflecting surfaces of these two minor units, the light passes through the imaging lens 33 and converges on the light-receiving surface of the detector 34, causing an interference. The intensity of the interference light received by the detector 34 is sent to the processer of a control system (not shown) and is Fourier-transformed by the computation processor, after which a spectral characteristic is obtained.

The object S to be measured has various textures on its surface, and the distribution of the amount of interference light on the imaging plane of the imaging lens 35 varies depending on the variation in the diffraction angle due to those textures. Furthermore, in the case of a spatially coherent light, no higher-order light will be generated from the surface of an object which has practically no texture, but only the zeroth-order light results. For example, in the case of Koehler illumination, the zeroth-order light reaches the objective lens 36 in the form of a collimated beam and converges on the optical Fourier-transform plane, so that it is impossible to divide the wave front by the transmissive phase shifter. However, by superposing a periodic texture on the surface of the object S, a distribution of the diffraction light can always be obtained on the optical Fourier-transform plane without being affected by the texture of the object surface, so that the phase-shift interference by the wave-front division can be constantly produced.

However, it is impossible to physically form a periodic structure on the surface of the object S. Accordingly, in the present embodiment, the conjugate plane imaging optical system is provided to optically form a conjugate plane of the object S, and additionally, a phase-type diffraction grating, which is a transmissive periodic structure, is placed on the conjugate plane to superpose a periodic texture on the conjugate plane. By this configuration of the present embodiment, the measurement light can be divided into two beams and made to interfere with each other regardless of the texture of the surface of the object S, so that a spectral characteristic can be obtained.

An interference light with an even higher visibility will be obtained if the amount of phase difference given to the measurement light by the phase-type diffraction grating satisfies the following condition: the amount of the continuously given phase difference between any two positions separated by a relative distance of $d=0.61\lambda/NA$ is equal to $\pi$ (rad.). For example, in the case of obtaining a two-dimensional spectral characteristic, a phase-type diffraction grating which can give a relative phase difference of $\pi$ between the neighboring bright points as shown in FIG. 13 should be used.

Figure 14:
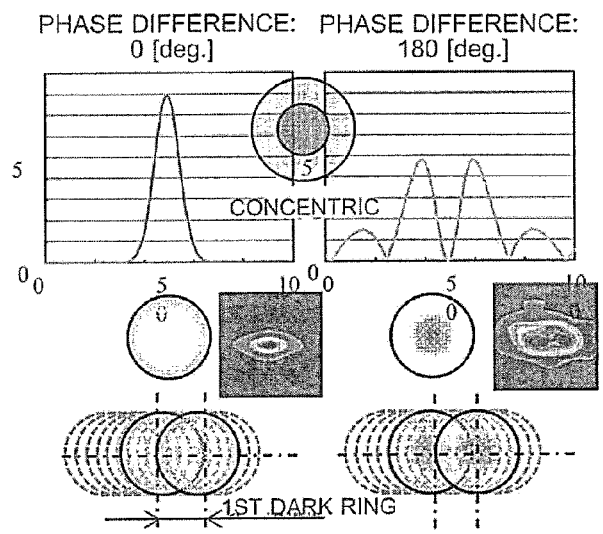
FIG. 14 is an explanatory diagram of the Fraunhofer diffraction.

The reason for giving a phase difference of $\pi$ (rad.) under the previously described condition is hereinafter described with reference to FIG. 14.

First, the group of consecutive bright points are divided into bright-point pairs, with each bright point having a radius $d=0.61\lambda/NA$ from the center of the convergence limit to the first dark ring ($\lambda$: wavelength of light; NA: numerical aperture). That is to say, the surface of the object S is supposed to be covered with consecutively arranged bright-point pairs separated by distance d. As is commonly known as the resolution limit of the Rayleigh criterion, each single bright-point pair consists of two bright points which have their brightness centers of the convergence limit and first dark rings mutually superposed. The distribution of the light intensity in each bright point changes with the phase-shifting operation, based on the Fraunhofer diffraction as a diffractive phenomenon of multiple beams passing through a lens aperture. In other words, if the amount of phase shift is zero, the interference occurs according to the normal convergence limit; i.e. the condition of the constructive multi-beam interference is satisfied at the bright-point center, making this center bright, while the condition of the destructive interference is satisfied at the first dark ring, making this ring dark. However, the phase difference of the beams changes with the phase-shifting operation, causing a change in the interference condition, so that the bright point makes a transition toward the condition of the destructive interference and becomes darker. Concurrently, the first dark ring makes the opposite transition, from the initial condition of the destructive multi-beam interference toward the condition of the constructive interference, and becomes brighter.

A simplified interpretation of this phenomenon is that, if the interference condition is macroscopically modelled, there is a difference of $\pi$ in the phase condition between the center of convergence and the first dark ring. That is to say, with the phase-shifting operation, the two bright points forming one pair mutually cancels their amounts of phase difference, and therefore, no change in the interference intensity can be observed in a low spatial-frequency region where the mutually cancelling bright-point pairs are consecutively arranged. However, at the edge portion, the interference intensity associated with the phase shift can be observed, since there is no longer any bright point to be the counterpart of mutual cancellation. Thus, the change in the interference intensity can be observed only at the edge portion.

The present invention is not limited to the previously described embodiments but can be appropriately changed.

For example, the transmissive phase shifter 13 may be configured so that the exit face of the second transmissive part 132 is inclined relative to that of the first transmissive part 131 while the entrance faces of the first transmissive part 131 and the second transmissive part 132 lie on the same plane.

Figure 15:
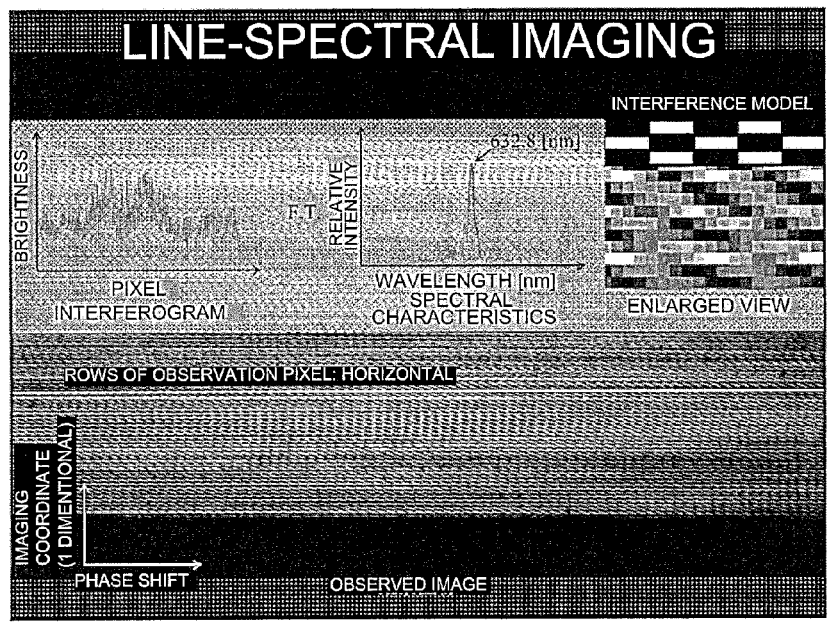
FIG. 15 is an image observed in a line-spectral imaging in which a slit and a phase-type diffraction grating were placed on the conjugate plane and a laser light was used as the light source.

Next, an example in which the present invention was applied in a line-spectral imaging is described. FIG. 15 is an image observed in a line-spectral imaging in which a slit and a phase-type diffraction grating were placed on the conjugate plane and a laser light (wavelength: 632.8 nm) was used as the light source. The horizontal axis of this observed image is the amount of phase shift and the vertical axis is the coordinate in the imaging direction. The upper left graph in the figure shows one example of the distribution of the brightness values of the pixels forming one horizontal row in the observed image. This is an interferogram of a single bright point (pixel) on the imaging line. By mathematically Fourier-transforming this interferogram, a clear spectral characteristic having a peak value of the line spectrum at a wavelength of 632.8 nm has been obtained (the graph at the center of the upper part in the figure). An enlarged partial view of the planar distribution of the interference intensity has confirmed that a houndstooth distribution of the interference intensity has been observed as theoretically predicted (the upper right image in the figure).

Figure 16:
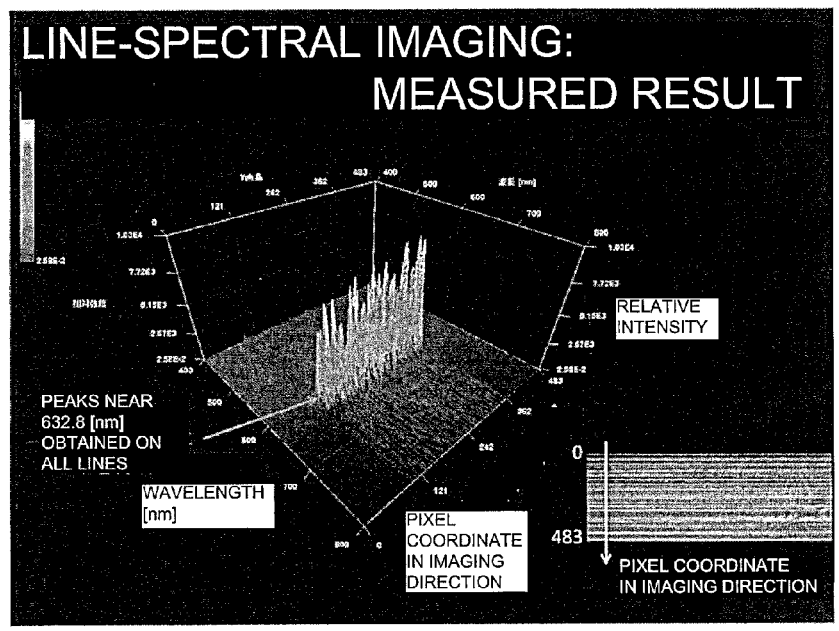
FIG. 16 is a three-dimensional graph showing the spectral characteristics on the imaging line obtained by Fourier-transforming horizontal interferograms on all the rows.

FIG. 16 is a graph showing a spectral characteristic on the imaging line obtained by Fourier-transforming the horizontal interferograms of all the rows. This is a three-dimensional graph of the relative spectral intensity distribution on the imaging line, where the coordinates on the bottom plane of the graph respectively indicate the wavelength and the pixel coordinate in the imaging direction, while the vertical axis indicates the relative intensity. As shown, a bright-line spectrum (peak wavelength: 632.8 nm) has been measured at every pixel coordinate on the imaging line.

Figure 17:
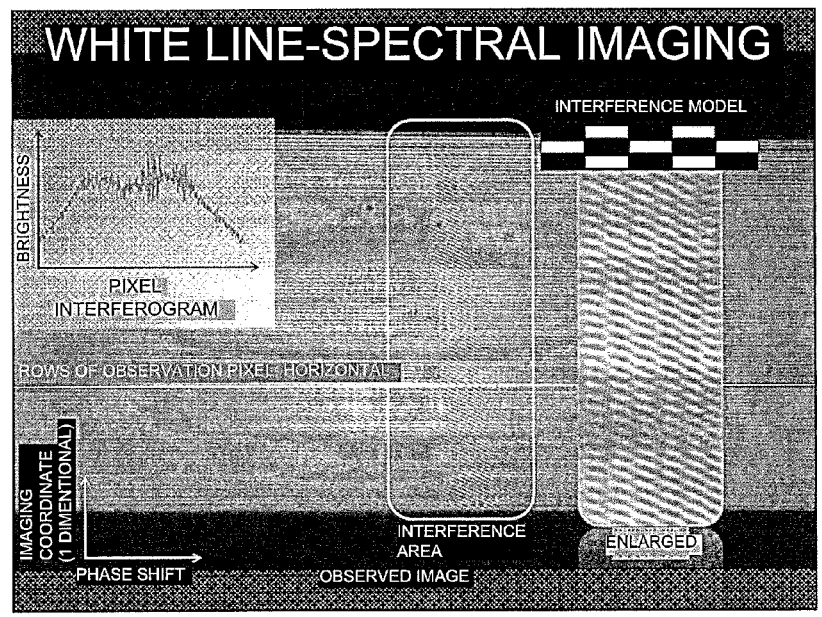
FIG. 17 is an image observed in a line-spectral imaging in which a slit and a phase-type diffraction grating were placed on the conjugate plane and white light (a metal halide lamp) was used as the light source.
Figure 18:
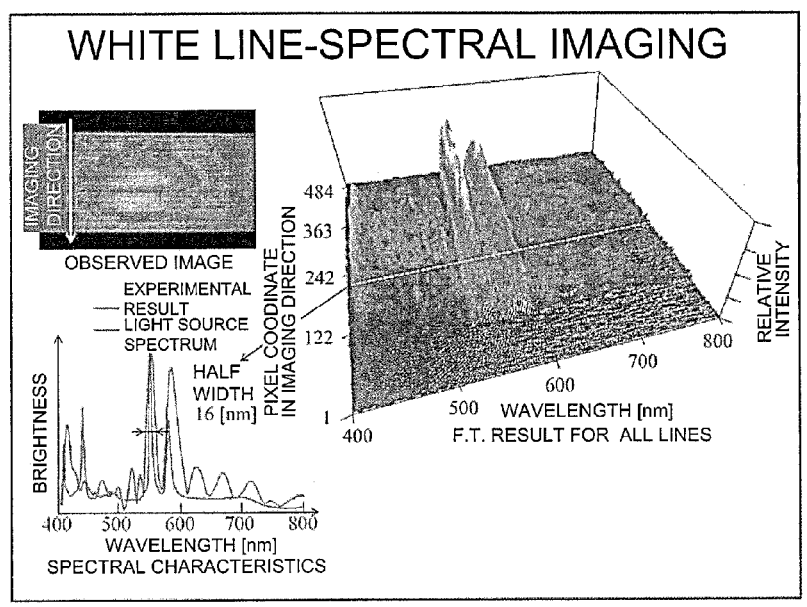
FIG. 18 is a three-dimensional graph showing a relative spectral intensity distribution obtained from horizontal interferograms by Fourier transform at all the pixels on the imaging line.

FIG. 17 shows an image observed in a line-spectral imaging in which a slit and a phase-type diffraction grating were placed on the conjugate plane and white light (a metal halide lamp) was used as the light source. FIG. 18 is a three-dimensional graph showing a relative spectral intensity distribution obtained by Fourier transform from the horizontal interferograms at all the pixels on the imaging line. This is a three-dimensional graph of the relative spectral intensity distribution on the imaging line, where the coordinates on the bottom plane of the graph respectively indicate the wavelength and the pixel coordinate in the imaging direction, while the vertical axis indicates the relative intensity. As shown, a spectrum having a plurality of bright lines specific to the metal halide lamp has been successfully measured.

These spectral distributions on the imaging line are spectral distributions at the limited depth corresponding to the focusing plane on the sample surface. A tomographic spectral imaging can also be performed by changing the position of the focusing plane in the depth direction.

Fifth Embodiment

In the configurations described in the third and fourth embodiments, a phase-type diffraction grating is used as the periodicity providing means. In the present embodiment, an amplitude-type diffraction grating is used as the periodicity providing means.

Figure 19:
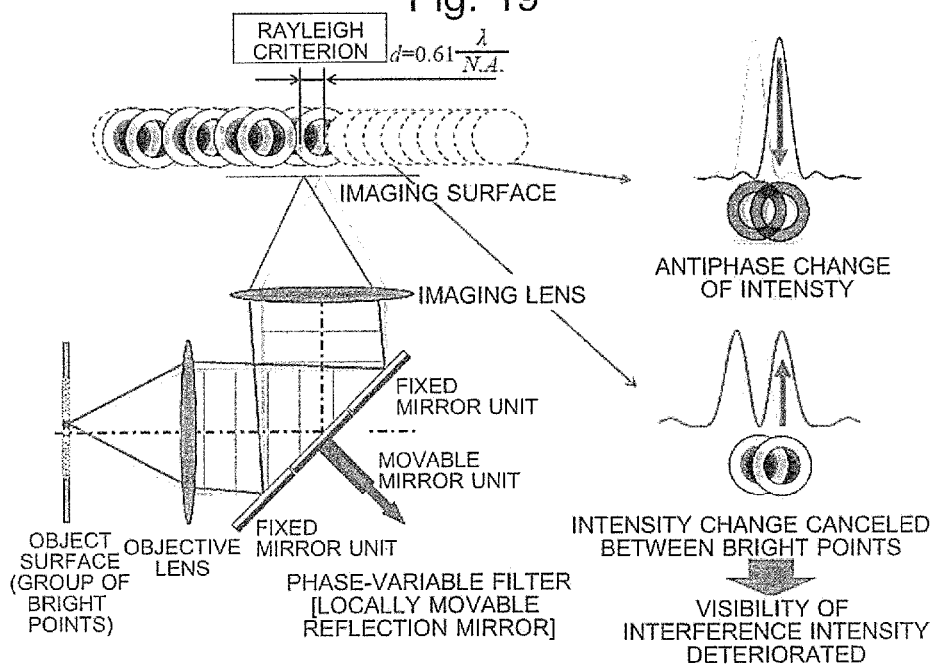
FIG. 19 is a diagram illustrating the visibility of the interference intensity in the case where a phase-type diffraction grating is used.

As described in the fourth embodiment, pairs of bright points whose radius d from the center of the convergence limit to the first dark ring is given by $d=0.61\lambda/NA$ are consecutively arranged at intervals of d on the surface of the object S. In the configuration using a phase-type diffraction grating, as shown in FIG. 19, each bright point has a counterpart bright point located at distance d from it, with the first dark ring of the latter bright point lying on the center of the former bright point. As a result, the neighboring bright points mutually cancel their respective changes in the intensity and may possibly deteriorate the visibility of the interference intensity.

Figure 20:
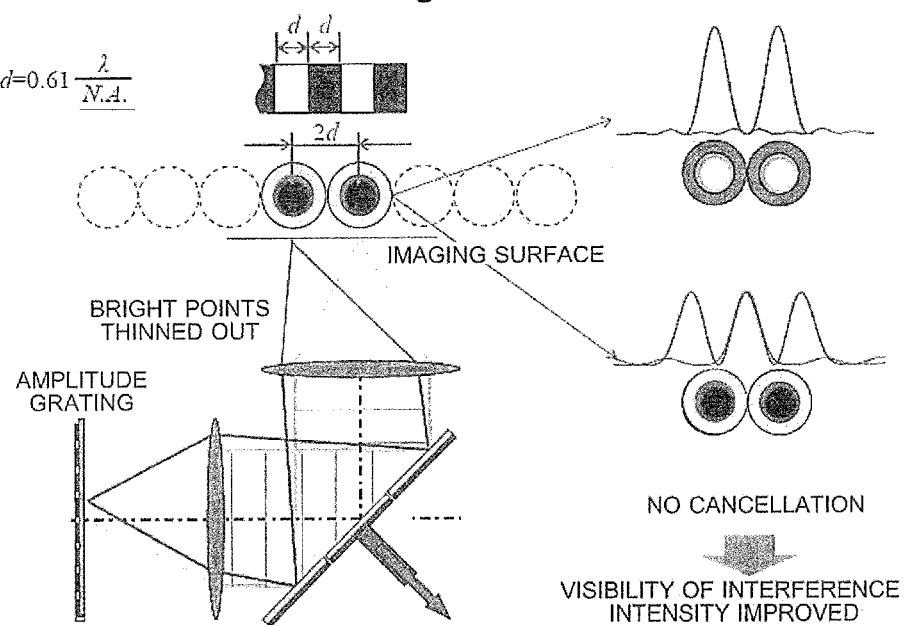
FIG. 20 is a diagram illustrating the visibility of the interference intensity in the case where an amplitude-type diffraction grating is used.

Given this problem, in the present embodiment, an amplitude-type diffraction grating is used, as shown in FIG. 20, to extract the alternate bright points arranged at intervals of d on the surface of the object S and increase the bright-point intervals to 2d. This prevents the interference visibility from deteriorating due to the cancellation of the intensity change among the bright points.

Figure 21:
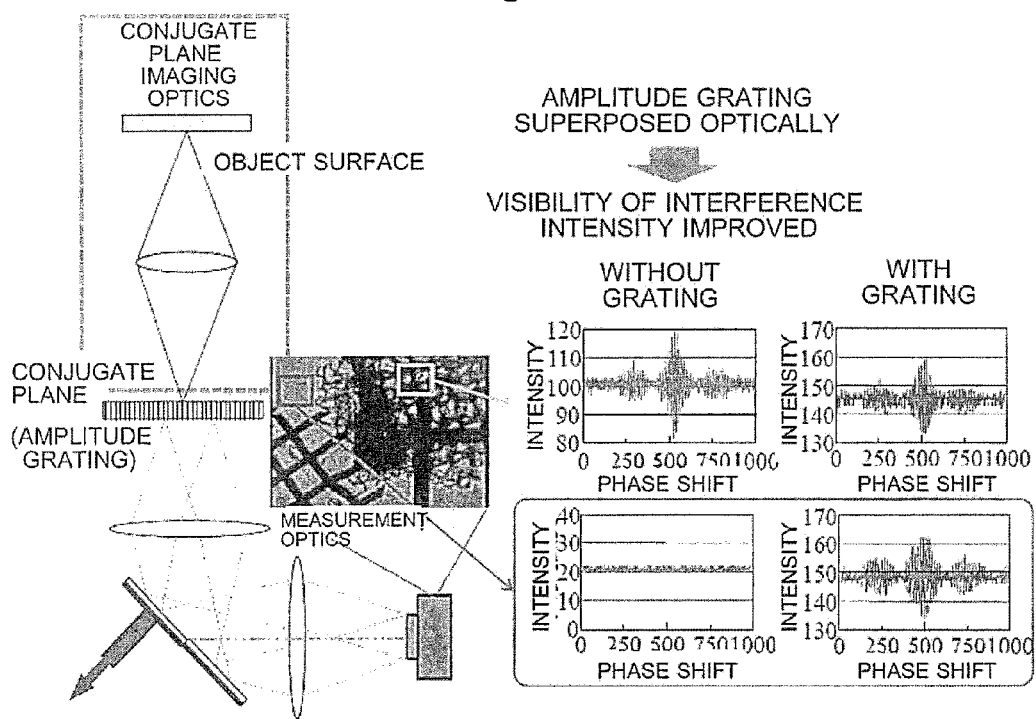
FIG. 21 is a schematic configuration diagram of a spectroscopic measurement device according to the fifth embodiment of the present invention, and a measured result obtained by the configuration of the fifth embodiment.

The left part of FIG. 21 is a schematic configuration diagram of the spectroscopic measurement device according to the fifth embodiment. Similarly to the fourth embodiment shown in FIG. 13, the device consists of a conjugate plane imaging optical system and a measurement optical system (2D-Fourier spectroscopic imaging optics). As already noted, the present configuration is identical to the fourth embodiment except the use of an amplitude-type diffraction grating as the periodicity providing means. Accordingly, descriptions on the individual components will be omitted.

A common feature of the spectroscopic measurement device of the fourth and fifth embodiments is that it is only the conjugate plane imaging optical system that needs to be individually designed for each measurement target; as for the two-dimensional Fourier spectroscopic imaging optics including the conjugate plane super-resolution grating (amplitude-type diffraction grating), the same optical system can always be used. This is because all that is needed is to set the magnification of the conjugate plane imaging optical system so that the real image on the conjugate plane will always have the same size.

The numerical aperture (NA) of the objective lens of the conjugate plane imaging optical system is determined from the resolution required for the target concerned. The magnification of the conjugate plane imaging optical system, and hence the choice of the imaging lens, is determined from the required size of the field of view and the size of the real image on the previously set conjugate plane. In the present embodiment, an amplitude-type diffraction grating with a grating period of 5 µm was used, with the aim of achieving a spatial resolution of 1 µm, which is the theoretical of two-dimensional Fourier spectroscopic imaging optics (with an objective-lens NA of 0.42 and a magnification of 5). The field of view was defined as 3.5×2.6 mm and the resolution was set at 2 µm. Accordingly, the magnification of the conjugate plane imaging optical system was 2.5 and the NA of the objective-lens was 0.196. A monochrome camera module (manufactured by Sony under model number XC-77, with a pixel size of 11 µm) was used as the photo-receiving device and a metal halide lamp (manufactured by SIGMAKOKI CO., LTD. under model number IMH-250) as the white light source.

In the present embodiment, a sample including a variety of spatial frequencies within the observation field was prepared and its spectral characteristics were measured. Specifically, an area with an extremely low spatial frequency and an area with an appropriately changing spatial frequency were formed by randomly putting fine fibers on a non-textured glass plate, and the spectral characteristics of each of those areas were measured ("With Grating" in the right part of FIG. 21). For comparison, interferograms were also obtained under the conventional configuration without using the diffraction grating ("Without Grating" in the right part of FIG. 21).

The amplitude value of the interferogram should preferably be uniform and independent of the spatial frequency. In the case of the conventional configuration where the amplitude-type diffraction grating was not used, no interference occurred on the non-textured area. By contrast, in the case of the configuration of the present embodiment, an interference occurred also in the non-textured area.

The spectroscopic measurement device according to the present invention cannot only be applied in medicine for a measurement of biological components such as blood sugar and blood cholesterol, but also in other various fields. For example, it can be used to measure the spectral characteristics of a material and test it for a defect in industrial fields, or to measure the spectral characteristics of a printed material in the field of scientific criminal investigation.

REFERENCE SIGNS LIST

11 . . . Case
   111 . . . Window
12, 31 . . . Objective Lens
13 . . . Transmissive Phase Shifter
   131 . . . First Transmissive Part
   132 . . . Second Transmissive Part
14 . . . Cylindrical Lens
15 . . . Two-Dimensional Array Device
16 . . . Inner Case
21 . . . Relay Lens
22, 37 . . . Phase-Type Diffraction Grating
32 . . . Reflective Phase Shifter
33, 35 . . . Imaging Lens

The invention claimed is:

1. A spectroscopic measurement device, comprising:
   a) a transmissive optical member composed of a first transmissive part having an entrance face and an exit face parallel to each other and a second transmissive part located next to the first transmissive part and having an entrance face and an exit face one of which is sloped relative to the other, with either the entrance face or the exit face of the second transmissive part lying on a same plane as either the entrance face or the exit face of the first transmissive part;
   b) an objective lens for collimating a measurement beam emitted from each of a plurality of measurement points located within a measurement area of an object to be measured and for making the collimated beam enter the first transmissive part and the second transmissive part;
   c) a cylindrical lens having an axis parallel to a line of intersection of the entrance face of the first transmissive part and a boundary surface between the first transmissive part and the second transmissive part, for receiving a first measurement beam exiting from the first transmissive part and a second measurement beam exiting from the second transmissive part;
   d) a detector, including a plurality of pixels, that detects an intensity distribution of an interference light produced from the first measurement beam and the second measurement beam entering the cylindrical lens; and
   e) a processor for acquiring an interferogram of the measurement points of the object to be measured based on the intensity distribution of the interference light detected by the detector, and for Fourier-transforming the interferogram to obtain a spectrum.

2. The spectroscopic measurement device according to claim 1, further comprising a tubular case for containing the objective lens, the optical member, the cylindrical lens and the detector in a linearly arranged form, the tubular case having a window formed at an end portion where the objective lens is located, and the window forming an entrance for a measurement beam emitted from a measurement point of the object to be measurement.

3. The spectroscopic measurement device according to claim 2, comprising an inner case for containing the optical member and the cylindrical lens, the inner case fitted in the tubular case in a rotatable manner.

4. The spectroscopic measurement device according to claim 3, comprising a drive means for rotating the inner case.

5. The spectroscopic measurement device according to claim 2, wherein the objective lens is fitted in the tubular case in such a manner as to be capable of moving along an optical axis.

6. The spectroscopic measurement device according to claim 3, wherein the objective lens is fitted in the tubular case in such a manner as to be capable of moving along an optical axis.

7. The spectroscopic measurement device according to claim 4, wherein the objective lens is fitted in the tubular case in such a manner as to be capable of moving along an optical axis.

* * * * *